United States Patent [19]

Ostensen et al.

[11] Patent Number: 5,601,085
[45] Date of Patent: Feb. 11, 1997

[54] ULTRASOUND IMAGING

[75] Inventors: Jonny Ostensen; Morton Eriksen; Lars Hoff; Sigmund Frigstad; Nils Sponheim; Knut Dyrstad, all of Oslo, Norway

[73] Assignee: Nycomed Imaging AS, Oslo, Norway

[21] Appl. No.: 538,286

[22] Filed: Oct. 2, 1995

[51] Int. Cl.$^6$ ........................................... A61B 8/00
[52] U.S. Cl. ........................ 128/662.02; 128/898
[58] Field of Search .............. 128/660.02, 660.05, 128/660.07, 661.01, 661.07, 661.08, 662.02, 898

[56] References Cited

U.S. PATENT DOCUMENTS 5,487,390  1/1996  Cohen et al. .................. 128/662.02

*Primary Examiner*—George Manuel
*Attorney, Agent, or Firm*—Bacon & Thomas

[57] ABSTRACT

Temporal variations in backscatter from an ultrasound contrast agent located in the vascular system and induced by movement of the scatterers are used to visualise the presence of contrast agent by determining areas where correlation between successive ultrasound images is poor. This low level of correlation arising from intravascular contrast agent movement permits distinction between stationary bulk tissue and moving bulk tissue since movement of the latter solid tissue scatterers is correlated.

8 Claims, No Drawings

ULTRASOUND IMAGING

FIELD OF THE INVENTION

This invention relates to ultrasound imaging, more particularly to methods of imaging the vascular system of a human or animal subject which permit generation of enhanced images of body tissues and fluids, e.g. blood.

BACKGROUND OF THE INVENTION

It is well known that ultrasound imaging is a valuable diagnostic tool, for example in studies of the vascular system, which term used herein embraces both vasculature and microvasculature as well as tissue penetrated thereby. Specific applications include cardiography and studies of tissue microvasculature. Such imaging is based on penetration of ultrasound waves, e.g. in the frequency range 1–10 MHz, into the subject, the waves interacting with interfaces of body tissues and fluids. Contrast in an ultrasound image derives from differential reflection and absorption of the ultrasound waves at such interfaces. Thus, for example, reflected waves may be analysed to give "grey-scale" images representing such interfaces on an appropriate visual display unit; Doppler techniques may be used to evaluate blood flow, information regarding which may, for example, be superimposed in colour upon such a grey-scale image.

It has long been recognised that contrast agents may advantageously be used to increase the difference in acoustic properties between different tissues and/or fluids, such agents typically being administered by intravenous injection when vascular studies are to be performed. Numerous contrast agent formulations have been proposed over the last 25 years, including emulsions, solid particles, water-soluble compounds, free gas bubbles and various types of encapsulated gas-containing systems; it is, however, generally accepted that low density contrast agents which are easily compressible are particularly efficient in terms of the acoustic backscatter they generate, and particular interest has therefore been shown in gas-containing and gas-generating systems.

Representative examples of such systems include gas-containing microparticulate contrast agents, for example as described in U.S. Pat. No. 4,442,843, EP-A-0122624, EP-A-0123235, DE-A-3834705, WO-A-9221382, WO-A-9300930, WO-A-9313802, WO-A-9313808 or WO-A-9313809; protein-encapsulated gas- or gas precursor-containing contrast agents such as Albunex® or as described in, for example, WO-A-9217213, WO-A-9406477 or WO-A-9501187; polymer- and other synthetic material-encapsulated gas- or gas precursor-containing contrast agents, for example as described in EP-A-0398935, EP-A-0458745, WO-A-9217212, WO-A-9317718, WO-A-9506518 or WO-A-9521631; systems employing gases selected to exhibit long term stability in vivo, for example as described in U.S. Pat. No. 5,413,774 or WO-A-9305819; and liposomal gas-containing systems, for example as described in U.S. Pat. No. 5,228,446 or U.S. Pat. No. 5,305,757. The contents of all of the foregoing documents are incorporated herein by reference.

Such contrast agents intended for administration by intravenous injection are typically designed to generate gas microbubbles having sizes in the range 1–10 μm or less, e.g. 1–7 μm, in order to ensure free passage through the capillary bed of the pulmonary system. Such microbubbles effectively act as point scatterers of ultrasound, and because of their random motion in fluids such as blood the backscatter which they generate will contain interference patterns due to interference between individual returning echoes. This phenomenon is termed speckle and typically produces a moving mottled effect in ultrasound images. The presence of such speckle is generally considered disadvantageous by virtue of the reduced image quality, and various techniques have been proposed for reducing speckle, for example as described in U.S. Pat. No. 5,409,007.

SUMMARY OF THE INVENTION

The present invention is based on the finding that temporal variations in the backscatter from an ultrasound contrast agent induced by movement of individual scatterers can be used as a valuable tool for detecting the presence of the agent, thereby permitting effective visualisation of contrast agent-containing tissue and/or fluids such a blood. The invention also facilitates discrimination between perfused and non-perfused tissue; thus lack of blood perfusion in particular tissue will be evident as lack of contrast, whilst subnormal perfusion will be indicated by delayed appearance of contrast following injection of contrast agent.

In principle any measurable function generated by the contrast agent may be employed, the presence of contrast agent being determined by analysis to detect areas where correlation between successive ultrasound images is poor, thereby denoting the presence of moving contrast agent moieties. It will be appreciated that such relative lack of correlation arising from intravascular contrast agent movement may readily be distinguished from bulk tissue movements since movement of solid tissue scatterers will be correlated.

Thus according to one aspect of the invention there is provided a method of imaging vasculated tissue of a human or non-human subject, said tissue containing an ultrasound contrast agent, which method comprises generating successive ultrasound images of said tissue, scanning a plurality of elements of each of said images for one or more image parameters, calculating correlation values in respect of said image parameter(s) for corresponding elements in said successive images, identifying any region or regions for which there is a change in said correlation values exceeding a defined level and generating a display of said region or regions.

DETAILED DESCRIPTION OF THE INVENTION

Ultrasound images which may be used in accordance with the invention include both two-dimensional images, including B-mode images of time-varying amplitude of the signal envelope, and individual scanlines, e.g. radio frequency ultrasound scanlines; the images are preferably analysed in digital form. Changes in correlation between successive images may, for example, be determined in time domain, frequency domain or intensity domain as appropriate.

To reduce the effects of movement, successive images of tissues such as the heart or kidney may be collected with the aid of suitable synchronisation techniques e.g. analogues to those used in ECG or respiratory movement recordings.

Thus, for example, a lack of intensity correlation factor $d_{i(l,k)}$ for pixel $(l,k)$ between images $i$ and $i-1$ may be determined from the relative difference in intensities $I_{i-1(l,k)}$ and $I_{i(l,k)}$ in pixel $(l,k)$ in images $i-1$ and $i$ by the formula (I)

$$d_{i(l,k)} = \omega d_{i-1(l,k)} + (1-\omega)\left|\frac{I_{i(l,k)} - I_{i-1(l,k)}}{I_{i(l,k)} + I_{i-1(l,k)}}\right|$$

where $\omega$ is a time or memory averaging factor such that $0<\omega<1$. Alternatively a similar correlation factor $d_{Ai(l,k)}$ can be determined from the absolute difference in intensities by the formula (II)

$$d_{Ai(l,k)} = \omega d_{Ai-1(l,k)} + (1-\omega)|I_{i(l,k)} - I_{i-1(l,k)}|.$$

It will be appreciated that the correlation factors will be large when intensity correlation from image to image is poor, so that regions where $d_{i(l,k)}$ exceeds a threshold value should be displayed in accordance with the invention. It may be advantageous first to average $d_{i(l,k)}$ over a region in space, e.g. a selected number of pixels, in order to improve the signal to noise ratio.

Alternatively, if a and b represent image intensities for corresponding two-dimensional areas in successive images, e.g. from rectangular arrays of a number of pixels, these areas having a centre point $(x_o, y_o)$ and a size of $\pm w$ pixels in the x and y directions, repeated calculations of an intensity correlation coefficient r may be made for a limited two-dimensional range $(\Delta x, \Delta y)$ using the formula (III)

$$r = \frac{\sum\limits_{x=-w}^{w}\sum\limits_{y=-w}^{w}(a_{x_0+\Delta x+x_1 y_0+\Delta y+y} - a_{mean})(b_{x_0+x_1 y_0+y} - b_{mean})}{\sqrt{\sum\limits_{x=-w}^{w}\sum\limits_{y=-w}^{w}(a_{x_0+\Delta x+x_1 y_0+\Delta y+y} - a_{mean})^2 \cdot \sum\limits_{x=-w}^{w}\sum\limits_{y=-w}^{w}(b_{x_0+x_1 y_0+y} - b_{mean})^2}}$$

where $$a_{mean} = \frac{\sum\limits_{x=-z}^{z}\sum\limits_{y=-z}^{z} a_{x_0+\Delta x+x_1 y_0+\Delta y+y}}{(2z+1)^2},$$

$$b_{mean} = \frac{\sum\limits_{x=-z}^{z}\sum\limits_{y=-z}^{z} b_{x_0+x_1 y_0+y}}{(2z+1)^2}.$$

These calculations permit identification of the local tissue movement vector, thereby allowing for elastic deformation of tissue. In the absence of moving intravascular contrast agent the peak value of r (i.e. $r_{max}$) is likely to be close to 1, but is reduced by the presence of contrast agent. The entire image may be scanned by varying $(x_o, y_o)$ and the resulting two-dimensional matrix of $r_{max}$ used to generate a display of the presence of intravascular ultrasound contrast agent, e.g. as a coloured or pseudo-coloured overlay image.

The images maybe spatially high pass filtered prior to the above-described calculations being made, in order to remove coarser tissue anatomical details while retaining the finer motion-induced variations in backscatter intensity, thereby enhancing the method's sensitivity in regions where tissue image details produce large grey-scale contrast. The use of high-pass filtered sets of images will also result in the values of $a_{mean}$ and $b_{mean}$ being close to zero, so that their calculation for each investigated region may be unnecessary, thereby speeding up the calculations.

One may also identify for each image elements such as pixels or groups of pixels which exhibit low correlation between their signal intensity and the signal intensity of adjacent elements, comparing results for successive images and generating a display of any regions where a threshold-exceeding change in correlation occurs.

It will be appreciated that correlation coefficients such as those disclosed above are dimensionless and that the calculations are inherently insensitive to absolute values. The method of the invention is accordingly insensitive to instrument parameters such as gain settings and to regional variations in image brightness and contrast introduced by instrumentation properties.

Where it is desired to determine changes in correlation in time domain one may, for example, use detection techniques involving correlation of successive radio frequency ultrasound scanlines, e.g. analogous to those disclosed in U.S. Pat. No. 4,803,990, the contents of which are incorporated herein by reference. Such techniques permit compensation for tissue movement by shifting the scanlines along the time axis until maximum correlation is achieved. Remaining variance will therefore be a measure of the presence of moving ultrasound contrast agent.

The intercorrelation function $f_i$ between two echographic lines $e_i$ and $e_{i+1}$ may be expressed by the formula (IV)

$$f_i(t_0, u) = \int_{t_0}^{t_0+w} e_i(t) e_{i+1}(t-u) dt$$

where $t_o$ is the ultrasound time of flight to the start of the region of interest and w is the length of the time window defining the region of interest. One may therefore determine the value of u (i.e. $u_{max}$) which maximises $f_i(t_0, u)$ for a selected region starting at $t_o$; the maximum value of $f_i(t_o, u_{max})$ may be used in combination with the total signal intensity or other parameters in respect of the same region for determining the presence of contrast. Thus low signal intensity may be interpreted as denoting blood without contrast agent, high signal intensity with high $f_i(t_o, u_{max})$ as denoting moving tissue without contrast agent and/or laminar flow of contrast agent-containing blood, and high signal intensity coupled with low $f_i(t_o, u_{max})$ as denoting tissue in which contrast agent is present and/or turbulent flow of contrast agent-containing blood.

It will be appreciated that in such techniques the pulse repetition frequency of the ultrasound beams may be adjusted to optimise detection of, for example, the presence of capillary flow and to discriminate this from tissue movement.

Changes in correlation by frequency domain methods may readily be based on parameters determinable in colour flow Doppler measurements, in particular signal power, mean frequency and bandwidth. Thus contrast agent-perfused regions will generate Doppler signals with a large ratio between bandwidth and mean frequency as a result of random movement of the scatterers coupled with non-uniform motion of blood through capillaries in such regions, this effectively representing a visualisation of lack of correlation between successive images of such regions.

Thus a Doppler signal exhibiting a large bandwidth:mean frequency ratio, i.e. in excess of a selected threshold value, together with strong signal power relative to blood backscatter level may be interpreted as denoting the presence of contrast agent-perfused tissue.

Multivariate methods such as principal component analysis, principal factor analysis, partial least square analysis or cluster analysis may, if desired, be used in conjunction with any of the above-described embodiments, permitting more comprehensive analysis of the ultrasound images. It will be appreciated that it may be preferable to analyse digitised image sequences stored on video or in other electronic storage media in preference to performing real time analyses of this nature.

A major advantage of the method of the invention is that whereas conventional ultrasound imaging requires that backscatter from a contrast agent must be stronger than backscatter from the surrounding tissue in order to register an intensity increase, the present method requires only that backscatter from the contrast agent be of the same order of strength as backscatter from surrounding tissue since this can be discounted by virtue of its high correlation between successive images. Consequently a smaller dose of contrast agent may be effective than is the case for systems based on conventional intensity imaging. Such lowered doses will decrease contrast-induced attenuation and so aid diagnosis of non-perfused or under-perfused tissues in deeply situated regions of the body.

The method of the invention my utilise any appropriate contrast agent, which will normally be administered by intravenous injection. Representative contrast agents which may be employed include any of the gas- or gas precursor-containing systems described hereabove.

The following non-limitative example serves to illustrate the invention:

EXAMPLE

In vivo imaging of a dog kidney

An anaesthetised dog was given an intravenous injection of 2 ml of a gas-containing microparticulate contrast agent (e.g. as described in WO-A-93/17718). After a 30 s delay contrast effects were. recorded using a Vingmed 750 ultrasound scanner at 5 MHz, with the transducer positioned above the location of the kidney. B-mode images were recorded at 0.5 s intervals. The images were post-processed by analogue to digital conversion into 180×180 pixel matrices. Subsequent calculations were performed using formula (III) above using a value of 5 for the parameter w. Correlation values of less than 0.7 were used to indicate perfusion. Perfused areas of the kidney were seen as distinct regions, appearing early in the cortical regions and later in the medulla.

We claim:

1. A method of imaging vasculated tissue of a human or non-human subject, said tissue containing an ultrasound contrast agent, which method comprises generating successive ultrasound images of said tissue, scanning a plurality of elements of each of said images for one or more image parameters, calculating correlation values in respect of said image parameter(s) for corresponding elements in said successive images, identifying any region or regions for which there is a change in said correlation values exceeding a defined level and generating a display of said region or regions.

2. The method of claim 1 wherein correlation values between successive images are determined in intensity domain.

3. The method of claim 1 wherein intensity parameters from a B-mode image are scanned.

4. The method of claim 1 wherein correlation values between successive images are determined by time domain analysis of radio-frequency scanlines.

5. The method of claim 1 wherein correlation values between successive images are determined by frequency domain analysis of radio-frequency scanlines.

6. The method of claim 1 wherein a gas-containing or gas precursor-containing ultrasound contrast agent is employed.

7. The method of claim 1 wherein correlation values are used in combination with total signal intensity or other image parameters in respect of the same elements to determine the presence of contrast.

8. The method of claim 1 wherein the display is stored using an electronic storage medium.

* * * * *